United States Patent [19]
Netzer

[11] Patent Number: 5,977,423
[45] Date of Patent: Nov. 2, 1999

[54] MIXED PHASE ETHYLATION PROCESS FOR PRODUCING ETHYLBENZENE

[76] Inventor: David Netzer, 1138 Hacienda Ct., Los Angeles, Calif. 90069

[21] Appl. No.: 09/175,643

[22] Filed: Oct. 20, 1998

Related U.S. Application Data

[60] Provisional application No. 60/089,968, Jun. 19, 1998.
[51] Int. Cl.$^6$ .................................. C07C 2/64; C07C 7/00
[52] U.S. Cl. ........................... 585/446; 585/804; 585/867
[58] Field of Search ..................................... 585/867, 804, 585/446

[56] References Cited

U.S. PATENT DOCUMENTS

| | | | |
|---|---|---|---|
| 3,426,088 | 2/1969 | Proctor, Jr. | 260/666 |
| 4,891,458 | 1/1990 | Innes et al. | 585/323 |
| 5,176,883 | 1/1993 | Smith, Jr. et al. | 422/211 |

FOREIGN PATENT DOCUMENTS

| | | |
|---|---|---|
| 1048385 | 1/1959 | Germany . |
| WO9809928 | 3/1998 | WIPO . |

*Primary Examiner*—Walter D. Griffin
*Assistant Examiner*—Thuan D. Dang
*Attorney, Agent, or Firm*—Christie, Parker & Hale, LLP

[57] ABSTRACT

An ethylbenzene production method is applied using a mixed phase ethylation of dilute ethylene with impure benzene. The benzene feed contains over 75% by weight benzene, with the balance being non-aromatic $C_6$ to $C_7$ hydrocarbons, including cyclohexane. The production method involves separating the benzene vapor from the hydrogen/methane rich vent gas by condensing the benzene at a temperature below about 5.5° C., the normal freezing point of benzene.

8 Claims, 2 Drawing Sheets

MIXED PHASE ETHYLATION PROCESS FOR PRODUCING ETHYLBENZENE

This application claims the benefit of U.S. provisional application No. 60/089,968, filed on Jun. 19, 1998.

FIELD OF THE INVENTION

The present invention is directed to an improved process for producing ethylbenzene.

PRIOR ART AND BACKGROUND OF THE INVENTION

Ethylbenzene, $C_8H_{10}$, is a key raw material in the production of styrene and is produced by the ethylation reaction of ethylene, $C_2H_4$, and benzene $C_6H_6$ in a catalytic environment. Old ethylbenzene production plants, typically built before 1980, used $AlCl_3$ or $BF_3$ as acidic catalysts. The newer plants in general have been switching to zeolite-based acidic catalysts. The typical purity of the benzene feed, known as nitration grade benzene, is 99.9 wt %. The typical purity of the ethylene feed would exceed 99.9 mol %.

A significant source of crude benzene is pyrolysis gasoline ($C_5$ to $C_9$), which typically contains 55–75 wt % aromatics. Pyrolysis gasoline, produced in naphtha based or heavy liquid based olefin plants, contains 35–55 wt % benzene. About 35% of world's benzene production capacity originates from pyrolysis gasoline. Typically, after pyrolysis gasoline is hydrotreated for saturation of olefins and di-olefins, the pyrolysis gasoline (free of olefins and sulfur compounds) is exported to battery limits for aromatics extraction process. Pure benzene, 99.9 wt %, along with toluene and xylene, is a typical product of aromatic extraction.

Impure benzene, 94–98 wt %, which is a 75–83° C. atmospheric cut, can be recovered from hydrotreated pyrolysis gasoline by a simple fractionation process, as described in U.S. Pat. No. 5,880,320, the disclosure of which is incorporated herein by reference.

Three types of ethylation reactor systems are used for producing ethylbenzene, namely, vapor phase reactor systems, liquid phase reactor systems, and mixed phase reactor systems. In vapor-phase reactor systems, the ethylation reaction of benzene and ethylene is carried out at about 380–420° C. and a pressure of 9–15 kg/cm²-g. In most cases, these systems use ethylene feed in pure form as produced in conventional olefin plants. Dilute ethylene streams, about 10–15 vol %, as produced in fluid catalytic cracking (FCC) in petroleum refining, are converted to ethylbenzene using vapor phase reaction. One known facility was designed by Raytheon Engineers & Constructors and is operated by Shell Chemicals at UK. Similar facilities for FCC off-gases were built in China by Sinopec.

Vapor phase reactor systems comprise multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions (at times referred to in the industry as alkylation reactions), the formation of xylene isomers as trace products occurs by side reactions. This xylene formation in vapor phase can yield an ethylbenzene product with about 0.05–0.20 wt % of xylenes. The xylenes show up as an impurity in the subsequent styrene product, and are generally considered undesirable.

Additionally, traces of propylene may enter the system with the ethylene feed or are formed by catalytic cracking of non-aromatic impurities that may enter with the benzene feed. The presence of propylene results in the formation of isopropyl benzene, commonly known as cumene, which is very undesirable in the ethylbenzene at concentrations above 150 PPM. The cracking of non-aromatic impurities is accelerated by increasing the ethylation reaction temperature, and thus substantial cracking of non-aromatic impurities to propylene occurs if the ethylation or transalkylation reaction is at temperatures of above 300° C. and in presence of acidic catalyst. This may result in an unacceptable level of cumene in the ethylbenzene product.

In order to minimize the formation of PEBs, a stoichiometric excess of benzene, about 400–900% per pass, is applied, depending on process optimization. The effluent from the ethylation reactor contains 70–85 wt % of unreacted benzene, 12–20 wt % of ethylbenzene product and about 3–4 wt % of PEBs. The PEBs are converted back to ethylbenzene to avoid a yield loss.

The effluent of the ethylation reactor can undergo ethylbenzene product recovery by several multiple fractionation stages. Benzene can be recovered in a benzene recovery column by stripping and can be recycled to the ethylation reactor. Ethylbenzene product can be recovered in an ethylbenzene recovery column. DEB and TEB can be separated from heavier aromatics in a PEB column. The heavy aromatics can be diverted to the fuel oil system.

The DEB and TEB mixture proceeds to a transalkylation reactor system where stoichiometric excess (250–300%) of benzene reacts with DEB and TEB in vapor phase at about 420–450° C. About 60–70% of the PEB is converted to ethylbenzene per pass. The effluent product of transalkylation reactor consists of ethylbenzene, un-reacted benzene and unconverted PEBs. This transalkylated stream undergoes stabilization for light ends removal and is recycled to fractionation in the benzene column. The ultimate conversion of DEB and TEB to ethylbenzene is essentially 100%.

The boiling point of the xylene isomer trace products is very close to that of the ethylbenzene, and thus no practical separation is possible. The ethylbenzene product typically contains 500–2,000 PPM by weight of xylene isomers, as well as 1000–2,000 PPM by weight of benzene.

In recent years the trend in industry has been to shift away from vapor phase reactors to liquid phase reactors. Liquid phase reactors operate about 260–270° C., which is under the critical temperature of benzene, 290° C. One advantage of the liquid phase reactor is the very low formation of xylenes and oligomers. The rate of the ethylation reaction is lower compared with the vapor phase, but the lower design temperature of the liquid phase reaction usually economically compensates for the negatives associated with the higher catalyst volume. The stoichiometric excess of benzene in liquid phase systems is 150–400%, compared with 400–800% in vapor phase. However, due to the kinetics of the lower ethylation temperatures, resulting from the liquid phase catalyst, the rate of the chain reactions forming PEBs is considerably lower; namely, about 5–8% of the ethylbenzene is converted to PEBs in liquid phase reactions versus the 15–20% converted in vapor phase reactions. Transalkylation reaction, where polyethylated benzene reacts with benzene to form ethylbenzene, can occur in a liquid phase or vapor phase system. The liquid phase reaction temperature would be 230–270° C. The fractionation sequences and product recovery methods for liquid phase reaction systems are similar to those used in connection with vapor phase reactor systems.

In recent years, technology has been developed for the production of ethylbenzene from dilute ethylene streams by a mixed phase reactor. The demonstrated dilute ethylene stream sources are from petroleum refineries, fluid catalytic cracking operation (FCC). ABB Lummus Global and CDTech have developed a mixed phase process. Aside from ethylation reactors, the sequence of the ethylbenzene product recovery and transalkylation is similar to the conventional liquid phase reactor systems.

A potentially alternate source of dilute ethylene is described in a pending U.S. Pat. No. 5,880,320. The dilute ethylene stream is extracted from the demethanizer section of the ethylene plant at about 22–30 kg/cm$^2$-g. Dilute gas from ethylene plants may contains 7–25 mol % ethylene, and the bulk of the balance is methane and hydrogen. The propylene content is controlled at the ethylene source to remain below 20 PPM by volume.

The use of a liquid phase reaction system for dilute ethylene streams is not possible. Due to the high methane and hydrogen content in the ethylene stream, the bubble point temperature of the combined mixture of dilute ethylene and benzene is very low, lower than the activity temperature of the ethylation catalyst, and actually below the freezing point of benzene.

The reaction temperature of the mixed phase ethylation reactor is under the dew point of the dilute ethylene benzene mixture, but well above the bubble point. The diluents of the ethylene feed comprise hydrogen, methane and small amounts of ethane, and CO remains essentially in the vapor phase. The benzene in the reactor is split between vapor phase and liquid phase, and the ethylbenzene and PEB reaction products remain essentially in liquid phase.

In the alkylation and transalkylation of aromatic hydrocarbons, zeolite catalysts have been shown to be an adequate substitute for acidic catalysts, such as aluminum chloride ($AlCl_3$), boron trifluoride ($BF_3$), liquid and solid phosphoric acid, sulfuric acid and the like. For example, U.S. Pat. No. 2,904,607 shows alkylation of aromatics in the presence of a crystalline aluminosilicate having a uniform pore opening of 6 to 15 angstroms.

U.S. Pat. No. 3,641,177 describes an alkylation process wherein the catalyst has undergone a series of ammonium exchange, calcination and steam treatments. This catalyst would currently be described as an "ultrastable" or "steam-stabilized" zeolite Y catalyst.

U.S. Pat. No. 3,751,504 and 3,751,506 show transalkylation and alkylation over ZSM-5 type catalysts. Use of other medium-pore to large-pore zeolites are taught in U.S. Pat. Nos. 4,016,245 (ZSM-35), 4,046,859 (ZSM-21), 4,070,407 (ZSM-35 and ZSM-38), 4,076,842 (ZSM-23), 4,575,605 (ZSM-23), 4,291,185 (ZSM-12), 4,387,259 (ZSM-12), and 4,393,262 (ZSM-12) and European Patent Application Nos. 7,126 (zeolite omega) and 30,084 (ZSM-4, zeolite beta, ZSM-20, zeolite L).

Liquid phase alkylation is specifically taught using zeolite beta in U.S. Pat. No. 4,891,458 and European Patent Application Nos. 0432814 and 0629549. Novel dealuminized mordenites are described for these types of reactions in U.S. Pat. Nos. 5,015,797 and 4,891,448.

More recently it has been disclosed that MCM-22 and its structural analogues have utility in these alkylation/transalkylation reactions. U.S. Pat. Nos. 4,992,606 (MCM-22), 5,258,565 (MCM-36), 5,371,310 (MCM-49), 5,453,554 (MCM-56), and 5,149,894 (SSZ-25). Additionally Mg APSO-31 is described as an attractive catalyst for cumene manufacture in U.S. Pat. No. 5,434,326.

U.S. Pat. No. 5,176,883 describes an integrated ethylation fractionation in general without diluants for the ethylene feed. U.S. Pat. No. 5,043,506 describes the addition of n-$C_5$, n-$C_6$, and i-$C_6$ as a means for fractionation control in alkylation systems.

SUMMARY OF THE INVENTION

In one embodiment, the present invention is directed to an ethylbenzene production system comprising a reactor vessel, a vapor phase ethylene feed stream and a benzene feed stream entering the reactor vessel, and a product stream containing ethylbenzene exiting the reactor vessel. The reactor vessel has an ethylation section and a benzene stripping section, whereby integrated vapor and liquid traffic is maintained between the ethylation section and stripping section. Preferably the reactor vessel is a single unit, but can alternatively comprise a plurality of integrated units, so long as integrated vapor and liquid traffic is maintained between the integrated units.

Dilute ethylene streams at a typical concentration of 7–25 mol % and less than 20 PPM of propylene will react with benzene at temperatures of 155–195° C. and pressures of 22–30 kg/cm2-g to form ethylbenzene and small amount of PEBs. The benzene stripper generates an internal benzene traffic in the ethylation section of about 300–400% stoichiometric excess, but additional vapor traffic is generated by the heat of reaction. The external stoichiometric excess of benzene is on the order of 3–15% depending on purge rate, purge recovery, benzene losses to vent gas and formation of heavy aromatic product. The stripper's bottom product is essentially free of benzene and suitable for ethylbenzene fractionation.

Preferably the reactor vessel further comprises a rectifying section and a transalkylation section. Alternatively, the system can comprises a transalkylation section outside of the reactor vessel.

In a particularly preferred embodiment, the invention is directed to an ethylbenzene production system comprising a reactor vessel, a vapor phase dilute ethylene feed stream and a benzene feed stream entering the reactor vessel, and a product stream containing ethylbenzene exiting the reactor vessel. The reactor vessel has an ethylation section and a benzene stripping section, whereby integrated vapor and liquid traffic is maintained between the ethylation section and stripping section. The vapor phase dilute ethylene feed stream comprises ethylene in a concentration of from about 3 to 50 mol % based on the total concentration of the ethylene feed stream. The benzene feed stream comprises benzene and at least one non-aromatic compound, wherein the concentration of benzene in the benzene feed stream is from about 75% to about 100% by weight, based on the total weight of benzene and non-aromatic compounds.

The methods of the invention are particularly useful for the utilization of impure benzene, typically 94–98 wt %, with a balance of cyclohexane and other non-aromatics. The source of this impure benzene would be pyrolysis gasoline, after hydrogenation and fractionation. Because the temperatures of the ethylation and transalkylation reactions are below 300° C., no significant cracking of non-aromatic is occurs. Production of xylene is very minimal if any.

Conventional zeolitic and nonzeolitic catalysts, with formulations in the public domain, can be used. These catalysts have been traditionally used for cumene manufacturing in a temperature range of 150–180° C. In the cumene reaction, propylene reacts with benzene to form isopropyl benzene; however, impurities of ethylene are also known to react with benzene to form ethylbenzene. The non-aromatic impurities are allowed to build in the ethylation loop, prior to purging to a purge ethylation reactor. The economics of the assumed purge reactor would largely depend on the concentration of non-aromatic impurities in the benzene feed.

In another embodiment, the invention is directed to a method for enhancing the recovery of benzene from an impure benzene feed. Cyclohexane is included in the impure benzene feed. The temperature of the impure benzene feed is then reduced below the freezing point of benzene. Preferably the temperature of the impure benzene feed is reduced to a temperature ranging from about −6° C. to about 4° C., more preferably from about −5° C. to about 0° C. Preferably the weight ratio of non-aromatics to benzene in the impure benzene feed ranges from about 0.25 to about 0.7.

DETAILED DESCRIPTION OF THE INVENTION

Figure 1:
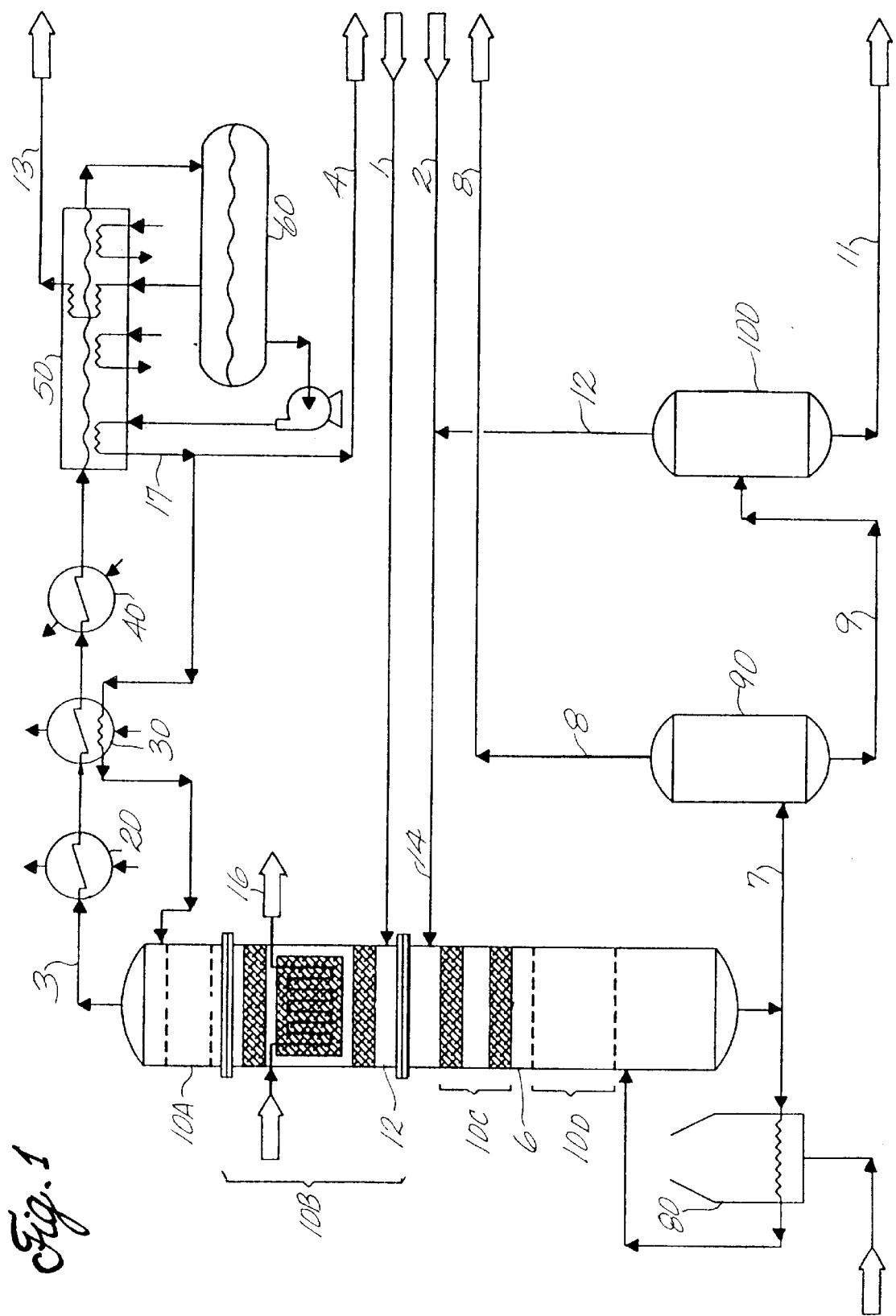
FIG. 1 illustrates one embodiment of the invention where the transalkylation catalyst beds are an integrated section of the overall ethylation reactor vessel.

One embodiment of an ethylbenzene production system according to the invention is depicted in FIG. 1. The ethylbenzene production system comprises a reactor vessel having several sections, namely an ethylation section, a transalkylation section, a rectifying section, and a stripping section. The reactor vessel, although depicted as a single vessel in FIG. 1, can be in the form of several integrated vessels, so long as the integrated vapor and liquid traffic is maintained between the ethylation and the stripping section.

The ethylation section, a fixed bed catalytic ethylation section, where vapor phase ethylene and mixed phase benzene feed streams react to form ethylbenzene and PEB, is an isothermal reactor. The heat of reaction and reboiler heat input to the system are recovered as 3–8 kg/cm²-g steam to be generated in the tubes. Additional steam at 1.5–2.0 kg/cm2-g would be generated at the overhead condenser. The dilute ethylene stream (containing methane and hydrogen) is introduced at the bottom of the catalytic ethylation section. The catalyst formulation is available at the public domain from cumene manufacturing technology. $AlCl_3$ catalysts, which are known to be active for ethylation reactions at about 150° C., could also be considered as a viable option for this system. Hydrogen, methane, vapor phase benzene and cyclohexane pass to the rectifying section, and ethylbenzene, PEB products, liquid phase benzene and heavy aromatics pass to the transalkylation section.

Fixed beds of catalyst will serve as transalkylator using a vapor liquid mixture of benzene and impurities such as cyclohexane, however no diluents of the ethylene feed the ethylbenzene and PEB will be essentially in liquid phase. The catalyst formulation for the transalkylation can be identical to the one used for the ethylation section. The heat effect of this reaction is nearly zero, and the operating temperature range would be 220–250° C. depending on the pressure. The stoichiometric excess of benzene in the transalkylation section is over 1000%, thus over 50 percent conversion of PEB to ethylbenzene per pass occurs for the end of run.

The remaining PEBs (after transalkylation), along with the ethylbenzene, benzene, and heavy aromatics proceed to the benzene stripping section. The stripping section is at the bottom of the reaction vessel and is the section where benzene stripping occurs. About 25 actual trays (15 theoretical) or equivalent packing can be used. Stripping duty is provided by a fired heater (or hot oil) providing thermal duty at about 295–325° C., depending on the pressure. The unreacted benzene along with cyclohexane is driven to the catalytic section, creating a localized excess of benzene, which improves reaction equilibrium to minimize PEB formation. The stripping heat input also increases the ethylation reaction temperature, thus improving the ethylation rate of reaction and minimizing the amount of catalyst required.

The upper section of the reactor vessel acts as a rectifier where reflux of benzene washes down the ethylbenzene vapors for full product recovery. Vent gas, depleted of ethylene, proceeds to residual benzene recovery by refrigeration.

In a preferred embodiment, a purge reactor similar to the one of the main reactor vessel described above, but without transalkylation section, could be included in the system. A purge stream from the ethylation loop with 60 to 85 wt % benzene (73% in the demonstrated case) reacts in a mixed phase with dilute ethylene. Because of the low benzene to ethylene ratio, the conversion of ethylbenzene to PEBs may reach 50% or more. The bottom of the stripping section consists of ethylbenzene 35–65 wt % and the balance is PEBs along with traces of benzene. This stream is routed to the feed of the ethylbenzene column as shown in FIG. 1.

The off gas from the purge reactor is chilled for benzene and cyclohexane condensation. The off-gas, rich in unconverted ethylene, proceeds to the ethylene feed stream of the main ethylation reactor. The residual, non-converted liquid resulting from the ethylation of the purge contains approximately 15–20 wt % benzene and the balance non-aromatics, principally cyclohexane. This liquid is disposed to the pyrolysis gasoline export, or to a crude cyclohexane facility.

Figure 2:
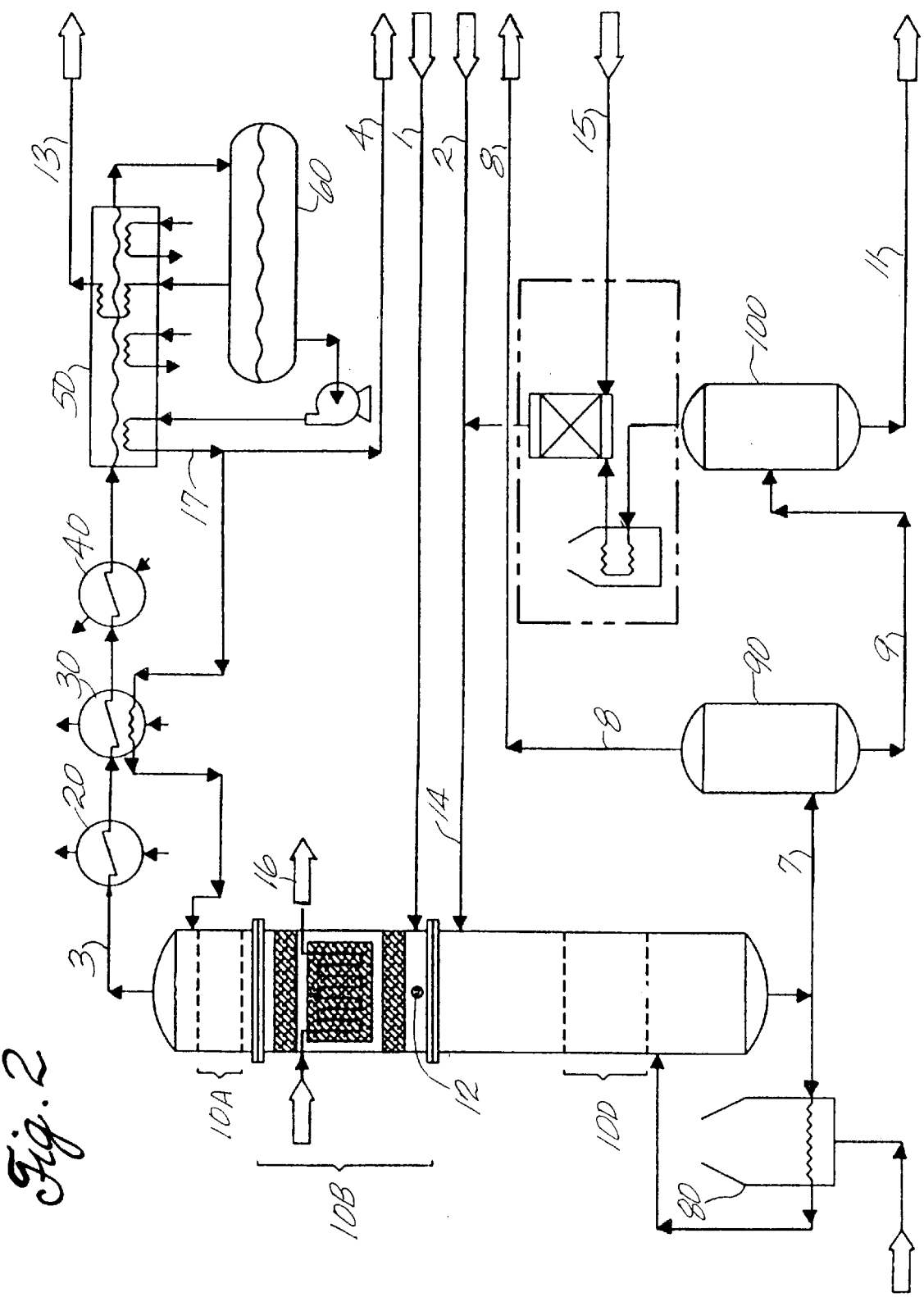
FIG. 2 illustrates an alternative embodiment of the invention where the transalkylation reactor is a liquid phase reactor and separated from the main reactor vessel.

In an alternative embodiment, as shown in FIG. 2, the transalkylation section is contained outside of the reaction vessel. This alternative design can be used if there is a concern of catalyst plugging and deactivation by heavy aromatics, or if the reaction is being run at a pressure below 20 kg/cm²g. The resulting operating temperature of below 220° C. would deactivate the catalyst.

When an impure benzene feed is used (for example, a feed originating from pyrolysis gasoline fractionation) the cyclohexane concentration builds in the upper rectifying section. The freezing points of pure benzene and cyclohexane are +5.5° C. and +6° C., respectively. The eutectic effect of cyclohexane buildup results in depression of the freezing temperature of the mixture to approximately −17° C. to −10° C. (depending on the ratio of benzene to cyclohexane). Thus, the benzene mixture from the rectifying section can be cooled to a temperature of −5° C. or lower. The lower temperature permits a greater amount of benzene recovery from the vent gas. Thus benzene recovery by refrigeration of the vent gas is a feasible approach, and the more conventional vent gas scrubber using PEB liquid can be avoided. For pure benzene feed, a conventional vent scrubber is required, unless cyclohexane is added to the overhead.

In U.S. Pat. No. 5,880,320, the usage of impure benzene is proposed in conjunction with hydrotreating and fractionation of pyrolysis gasoline in an adjacent olefin plant. Typically, this impure benzene resulting from pyrolysis gasoline includes about 2–6 wt % cyclohexane, depending on naphtha feed analysis and cracking severity in the olefin plant. The non-aromatic impurities also include traces of other $C_6$ and $C_7$'s. These impurities would be allowed to build to a weight ratio of 0.3–0.70 to the benzene in the reflux drum. The eutectic effect of the impurities will allow the chilling the vent gas to −2° C. to −10° C., becoming an economical way to recover residual benzene. Some non-aromatic impurities will escape with the vent gas, and most of it would be purged as liquid. This methodology is described in U.S. Pat. No. 5,880,320.

EXAMPLE

For illustration and consistency purposes, an ethylbenzene production system for 380,000 tonne per year of ethylbenzene is described. The streams and apparatus designations are depicted in FIG. 1. The assumed production rate is based on 345 operating days per year. The dilute ethylene feed (Stream No. 1) to the facility is originated from a naphtha based olefin plant. Stream No. 1, at a pressure of 25 kg/cm$^2$-g and a temperature of 30° C., has the following composition:

| Component | kg-mol/hr | Mol % |
| --- | --- | --- |
| Hydrogen | 1,460 | 31.1 |
| CO | 21.0 | 0.44 |
| Methane | 2748.0 | 58.6 |
| Ethylene | 448.0 | 9.6 |
| Ethane | 9.0 | 0.2 |
| Propylene | 0.02 | 5 PPM |
| Acetylene | 0.02 | 5 PPM |
| Total | 4686 | |

Stream No. 2 contains impure benzene from a pyrolysis gasoline source. More specifically, Stream No. 2 comprises:

| Component | kg/hr | kg-mol/hr | wt % |
| --- | --- | --- | --- |
| Benzene | 38,200 | 490 | 96.0 |
| Cyclohexane | 1,400 | 16.6 | 3.5 |
| Dimethyl pentanes | 160 | 1.6 | 0.4 |
| N-heptane and $C_6/C_7$ | Trace | Trace | Trace |
| Toluene | Trace | Trace | Trace |
| Water | Trace | Trace | 10 PPM |
| Sulfur Compounds | Trace | Trace | 0.5 PPM (as sulfur) |
| Total | 39,760 | 508 | |

At the end of the run, there is a total ethylene utilization 98% and 0.8% ethylene losses to heavy aromatics. Thus, 97.2% of the ethylene is converted to ethylbenzene, and the balance is routed to gaseous and liquid fuels. Impurities build up in the liquid of the reflux drum 60 is 27 wt %. The system does not contain a purge reactor. Ethylene enters the bottom of the ethylation catalyst bed and reacts with benzene in liquid phase at 180° C. The heat of reaction, 12 MM Kcal/hr, about 975 Kcal per kg of ethylene is mostly recovered by generating steam stream 16 and vaporizing benzene. The benzene is recondensed at the overhead and the vent gas chilling system 50. About 5.0% of the ethylbenzene formed in the ethylation catalyst beds further reacts with ethylene. About 3.8% of the ethylbenzene ends as DEB, 1.0% as TEB, and the balance, 0.2%, as heavier aromatics. The overhead of the ethylation catalyst beds contains hydrogen, methane, benzene and small amounts of ethylbenzene and unconverted ethylene. The overhead gas from the ethylation beds proceeds to the rectifying section, about 5 to 7 trays, where ethylbenzene is recondensed. Reactor vessel overhead gas stream 3 proceeds to condenser/steam generator 20, and steam at 2.0 kg/cm$^2$-g is generated. The gas is further cooled to about 65° C. by preheating tempered water at 30 from 50° C. about 80° C. The gas is further cooled to 35° C. with 30° C. water at 40. The vent gas at 35° C. is chilled at 50 to −5° C., by using +12° C. and −8° C. refrigeration, for example, from the nearby olefin plant. Liquid and vent gas products are separated in the reflux drum 60 and reheated to 30° C. by cold recovery at 50. Vent gas, stream 13, at 22 kg/cm$^2$-g and 30° C. proceeds to PSA hydrogen recovery (not shown) or to a fuel gas system at the following composition:

| | k-mol/hr | Mol % |
| --- | --- | --- |
| Hydrogen | 1,460 | 34.4 |
| Methane | 2,748 | 64.7 |
| Ethane | 9 | 0.2 |
| CO | 21 | 0.5 |
| Ethylene | 9 | 0.2 |
| Benzene | 4 | 0.1 |
| Cyclohexane | 1.2 | — |
| Ethylbenzene | Trace | — |
| PEB | Trace | — |
| Total | 4,252 | 100 |

A purge, stream 4, of 5,300 kg/hr of liquid from the reflux stream 17 drum containing 73 wt % benzene is drawn from the reflux line at 30° C. By applying the optional purge reactor (not shown) the overall yield of ethylbenzene from benzene increases from 88% to 97%. The benzene yield losses will show as pyrolysis gasoline if no purge reactor is applied.

Liquid bottom product from the ethylation section 10-B, stream 12, contains benzene; cyclohexane ethylbenzene and PEB descend to the transalkylation section 10-C along with recycle DEB and TEB. About 80% of the PEB is reconverted to ethylbenzene at the start of the run and 50% at the end of the run. The material balance is based on end of run and transalkylation at 235° C.

Transalkylated product line, internal stream 6, proceeds to the stripping section 10-D. Reboiler 80 provides the stripping duty of about 16 MM Kcal/hr. Bottom product, stream 7, results from benzene stripping and has the following composition:

| | kg/hr | kg-mol/hr | wt % |
| --- | --- | --- | --- |
| Ethylbenzene | 46,100 | 435 | 87.0 |
| DEB | 5,200 | 39 | 9.8 |
| TEB | 1,400 | 8.5 | 2.6 |
| Heavy | 130 | 0.6 | 0.25 |
| Benzene | 70 | 1.0 | 0.13 |
| Cyclohexane | 10 | 0.2 | 0.02 |
| Total | 52,910 | | |

The stripped product, stream 7, at 310° C., proceeds to the ethylbenzene column 90. The overhead from the ethylbenzene column, stream 8, is ethylbenzene product with 1,500 PPM of benzene and 250 PPM of cyclohexane.

The bottom product from the ethylbenzene column stream 9 contains:

| | |
|---|---|
| Ethylbenzene | 200 kg/hr |
| DEB | 5,200 kg/hr |
| TEB | 1,400 kg/hr |
| Heavy | 130 kg/hr |

This mixture, stream 9, proceeds to PEB column 100, where heavy aromatics, stream 11, are separated as bottom product. DEB and TEB overhead, stream 12, recycle to the transalkylation section 10-C.

In the conservative design, FIG. 2, the conversion in the transalkylator will be 60% at liquid phase reactor at about 270° C. About 3,500 kg/hr of DEB and TEB would react with about 10,000 kg/hr of pure benzene feed from stream 15. The material balance at FIG. 2 is somewhat different than FIG. 1 and not shown.

I claim:

1. A method for enhancing the recovery of benzene from a vent gas containing benzene during the production of ethylbenzene, the method comprising:

providing a benzene feed stream containing cyclohexane;

reacting the benzene feed stream with ethylene to produce ethylbenzene and a vent gas containing benzene, methane and cyclohexane;

reducing the temperature of the vent gas below 5.5° C. to condense the benzene without solid formation, whereby the cyclohexane suppresses the solid formation temperature of the mixture below the freezing temperature of the benzene; and converting condensed benzene to ethylbenzene.

2. A method according to claim 1, wherein the temperature of the vent gas is reduced to a temperature ranging from about –17° C. to about 4° C. without formation of the solids.

3. A method according to claim 1, wherein the temperature of the vent gas is reduced to a temperature ranging from about –10° C. to about –5° C. without formation of the solids.

4. A method according to claim 1, wherein the weight ratio of the cyclohexane to benzene in the vent gas ranges from about 0.25 to about 0.7.

5. A method for enhancing the recovery of benzene from a vent gas containing benzene during the production of ethylbenzene, the method comprising:

providing a benzene feed stream containing cyclohexane;

reacting the benzene feed stream with ethylene to produce ethylbenzene and a vent gas containing cyclohexane, methane and benzene;

reducing the temperature of the vent gas below the normal freezing temperature of benzene to condense the benzene, whereby the cyclohexane suppresses the solid formation temperature of the mixture; and converting condensed benzene to ethylbenzene.

6. A method according to claim 5, wherein the temperature of the vent gas is reduced to a temperature ranging from about –17° C. to about 4° C. without formation of the solids.

7. A method according to claim 5, wherein the temperature of the vent gas is reduced to a temperature ranging from about –10° C. to about –5° C. without formation of the solids.

8. A method according to claim 5, wherein the weight ratio of cyclohexane to benzene in the vent gas ranges from about 0.25 to about 0.7.

* * * * *